United States Patent [19]

Neumann

[11] Patent Number: 4,494,869
[45] Date of Patent: Jan. 22, 1985

[54] APPARATUS AND METHOD FOR PHOTOMETRIC MEASUREMENT OF OIL PRESENT ON HUMAN SKIN

[76] Inventor: Hans D. Neumann, 1011 Parma Way, Los Altos, Calif. 94022

[21] Appl. No.: 391,078

[22] Filed: Jun. 22, 1982

[51] Int. Cl.³ .................. G01N 1/10; G01N 33/26
[52] U.S. Cl. ........................... 356/36; 356/70; 356/244
[58] Field of Search ............. 356/38, 246, 432, 433, 356/434, 244, 70, 36

[56] References Cited
U.S. PATENT DOCUMENTS
2,059,374 11/1936 Logan et al. ................ 356/246
2,766,653 10/1956 Martin et al. ............ 356/434 X Primary Examiner—Vincent P. McGraw
Attorney, Agent, or Firm—Joseph H. Smith; Ronald E. Grubman

[57] ABSTRACT

A photometric skin condition analyzer is provided which exploits the light refraction and Rayleigh scattering from small particles, such as droplets of oil, deposited on optically smooth sampling surfaces of a sampling pellet. Light emitted from an optical source is passed through the sampling surface and focused onto an optical detector. The output signal of the detector is displayed to give an indication of the degree of oiliness of the skin.

5 Claims, 10 Drawing Figures

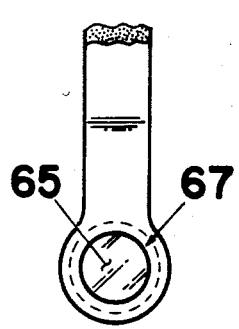
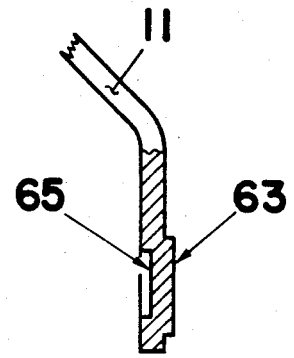
Fig. 6
Fig. 5
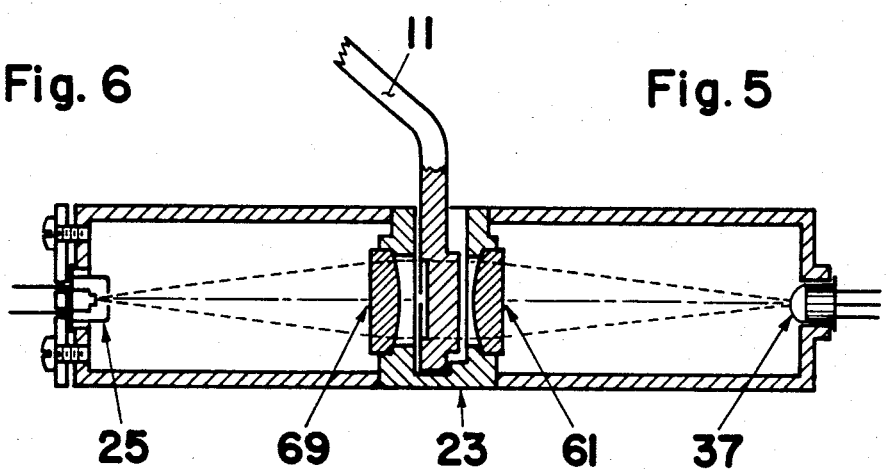
Fig. 7

APPARATUS AND METHOD FOR PHOTOMETRIC MEASUREMENT OF OIL PRESENT ON HUMAN SKIN

BACKGROUND OF THE INVENTION

The measurement of the natural presence of oil on the human facial skin is a problem of current interest among cosmetics manufacturers, since the quantitative assessment of skin oiliness enables the beautician or cosmetics sales clerk to recommend an optimal assortment of cosmetics to each individual customer.

It has been proposed in the prior art to perform the skin oiliness measurement by first contacting a ground glass in the form of a small sampling pellet to the subject's skin, and then detecting a change in the light-scattering properties of the groundglass. Prototype instruments based on this scheme have been constructed, which include a light-emitting diode (LED), and a silicon light detector placed within a small portion of the luminous emission field of the LED. The groundglass is inserted between the LED and the detector so that it intercepts some radiation from the LED. The principle of operation of these prior art devices relies on the fact that a clean groundglass with a specific surface texture exhibits a unique light scattering property in which the scattered light distribution as a function of the angle subtended by the detector surface is critically dependent upon the surface granularity of the groundglass. A clean, oil-free groundglass exhibits the highest light scattering, which results in minimal illumination of the detector and correspondingly low photocurrent. However, when a specimen of oil is applied to the groundglass, the amount of light scattered away from the incident beam direction is reduced so that slightly more light impinges on the detector. This produces a small increase of photocurrent from the detector, and the small difference between the photocurrent readings is the basis for the measurement.

Two major disadvantages and several practical shortcomings are associated with this method. First, the signal level is low, because the major portion of the light emitted from the LED does not fall on the detector. Thus, a very high gain of the signal amplifier is required in order to produce a useful indication. Electronic drift, stray light interference and temperature effects have become a significant source of error in the measurement. Second, the granular surface of the groundglass is difficult to reproduce with consistent properties, which makes the calibration of the measurement system problematic. If plastic is used for the sampling pellet to reduce its cost, contamination of the surface during manufacturing can cause high reject rates, since cleaning method have largely proved ineffective.

It has also been considered to make a plastic "groundglass" by injection molding, in order to produce low cost disposable pellets, which are a prerequisite for widespread application of this concept. However, experience has shown that mold deterioration of injection molding dies is proportional to the surface profile gradients and the number of parts made in the die. A finely textured mold surface is subject to abrasive wear from the recurrent injection of the plastic material, and the optical properties of the molded parts deteriorate early in a production run. The present invention eliminates the above-mentioned disadvantages and practical shortcomings by the use of a smooth optical surface. Such a surface can be molded in large production quantities without mold deterioration. By curving the surface to produce some positive refracting power, the light level at the detector is greatly increased, and the corresponding signal processing is simplified considerably.

SUMMARY OF THE INVENTION

According to the illustrated preferred embodiments, the present invention provides a photometric skin condition analyser, which exploits the light refraction and Rayleigh scattering from small particles deposited on optically smooth sampling surfaces of a sampling pellet. Light emitted from an optical source is passed through the sampling surface and focused onto an optical detector.

In preferred embodiments the sampling surface is either spherical, aspheric or flat and possesses an optically smooth finish. The instrumental arrangement in all preferred embodiments includes a source of visible or infrared radiation having a small emitting area, and a solid state detector, mounted opposite the emitter at a certain specified distance. In the space between emitter and detector there is a receptacle for the sampling pellet, which accurately locates the pellet between emitter and detector. In accordance with one embodiment of the invention the optical power of the sampling pellet and the component spacings are designed such that the sampling pellet forms an image of the emitting surface on the detector. This image may be of unity magnification or a magnification suitable to match the relative sizes of the emitting and detecting surface. Due to the lateral and longitudinal registration of the sampling pellet on the optical centerline, nearly all of the radiation intercepted by the pellet will be directed to fall upon the detector. The circuitry governing the emission level and the detector sensitivity is electronically stabilized, so that the optical transmission of the sampling pellet and the surface condition of same become the only significant variable in determining the signal level at the detector.

In operation, this signal level represents the calibration point for a "clean" sample. When one surface of the sampling pellet has been in contact with the skin, microscopic droplets of skin oil will have been transferred to the sampling surface, each forming a minute optical element, whose individual refractive and scattering effects cause a defocusing of the optical system. The smaller droplets will trap most of the light by total internal reflection, where the larger ones tend to destroy the optical figure of the sampling surface. Scattering occurs on the smaller droplets, and along with some absorption, the signal level at the detector is caused to fall essentially in correspondence with the amount of oil transferred to the sampling surface. With a clean sample, over 90% of the light intercepted by the sampling pellet reaches the detector, so that the signal level is high, and even a very small amount of oil on the sampling surface is detectable.

In another embodiment of the invention, the sampling pellet is made up as an optical flat, with zero refracting power. The instrument designed to use this kind of pellet contains, in addition to the aforementioned emitter and detector, a pair of lenses, functioning as collimator and objective lens, which take over the imaging function. Here, the space between the two lenses contains the receptacle for the sampling pellet. Since the light in this space is collimated, the lateral registration of the sampling pellet is uncritical. The effect of surface deposits on the flat sampling surface is the same as in the other preferred embodiments and yields the same quality of measurement.

DESCRIPTION OF THE DRAWINGS

FIG. 5 is a cross-section of another embodiment of the sampling pellet where both surfaces of the optical portion are flat.

FIG. 6 is a partial view of the sampling pellet, where one surface represents the aperture stop of the optical system.

FIG. 7 illustrates another preferred embodiment, in which the optical power is provided by fixed lenses inside the optical assembly and the sampling pellet has plano-parallel surfaces.

DETAILED DESCRIPTION OF THE INVENTION

Figure 1:
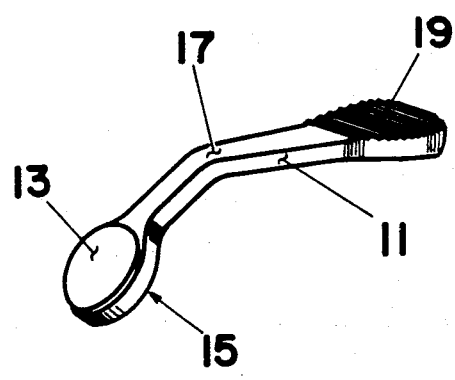
FIG. 1 shows a molded plastic sampling pellet and holder.

In FIG. 1 there is shown a sampling pellet, preferrably injection molded from optically clear acrylic, styrene or other suitable plastic. A sampling surface 13 is convex spherical or aspheric, while a back surface 15 may be spherical, aspheric or flat, depending on the optical configuration of an analyzing instrument for which the sampling pellet is designed. These two surfaces, along with the bulk material between them, form an optically refractive element, whose refractive power may vary from zero to some positive number, again depending on the instrumental optics. When sampling pellet 11 is inserted into a receptacle of the optical portion of an analyzing instrument, it becomes a part of an optical assembly, which is illustrated in FIG. 2, in one preferred embodiment.

Figure 2:
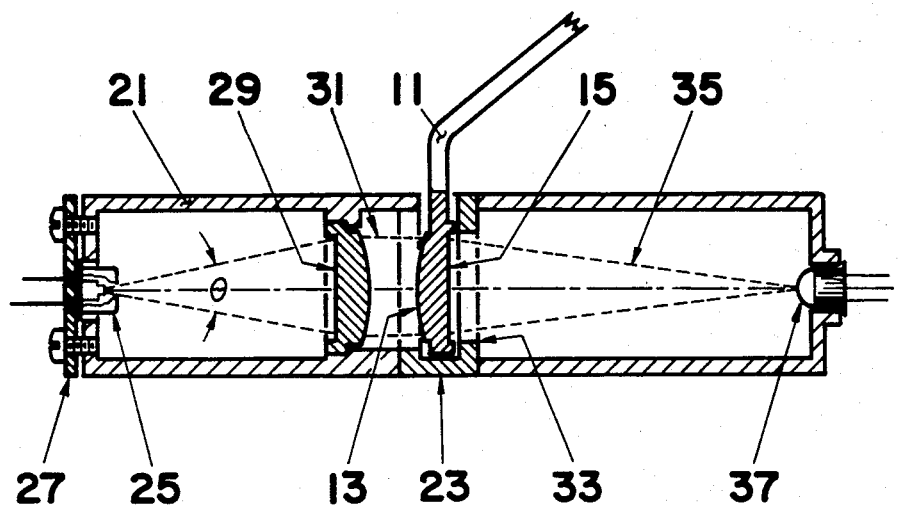
FIG. 2 illustrates one preferred embodiment of the optical system, in which the optical power is partly provided by a collimating lens, fixed in an analyzing instrument.

In FIG. 2, a housing 21 contains a receptacle 23 for the sampling pellet 11 whose optical surfaces 13 and 15 represent a sampling surface and a back surface, respectively. The sampling surface in this embodiment is spherical, while the back surface is flat. A solid state visible or infrared lamp 25 such as a number 55BF126 available from the General Electric Company, is mounted on a centering plate 27 of the housing 21. A collimator lens 29 is fixed in the housing at a distance from source 25 equal to its focal length. The collimator lens 29 intercepts radiation from the source 25 within the solid angle $\theta$ and sends it towards the right as a collimated beam 31. When no sampling pellet 11 is inserted in the receptacle 23, the collimated light propagates toward a detector 37 fixed in the center of the opposite end of the housing 21. The sensitive area of the detector is very small compared to the cross-section of the collimated beam, hence only a negligible amount of light is intercepted and the resulting photocurrent is minimal. Now, when the sampling pellet 11 is inserted into the receptacle 23, it intercepts the collimated beam 31. The receptacle 23 is arranged such that it locates the sampling pellet 11 on the centerline of the optical system, and at a distance from the detector 37 equal to the focal length of the refractive element in the sampling pellet holder. Thus, the collimated radiation from lens 29 is focused by the pellet 11 on the detector 37. It should be noted that if the detector 37 is positioned at a distance other than the focal length of the refractive element, the collimated radiation will still be converged onto the detector and the device will be operable; however the optimal position of the detector is as described above. A similar comment applies to the other embodiments described herein.

An aperture stop 33 provided as part of the receptacle 23 defines the exact cross-section of the convergent beam 35. Since all sampling pellets are produced in the same injection molding die, they will come to rest in the same location when inserted in the receptacle. In this way, the focus of the convergent beam 35 will be spatially fixed. The centering plate 27 allows the initial placement of the source 25 on the optical axis defined by collimator lens 29 and the detector 37. In this way, the optical system will remain aligned and will require no adjustment after the initial factory alignment. Understanding the details of this measurement system may be facilitated by reference to FIG. 3 and the following discussion.

Figure 3:
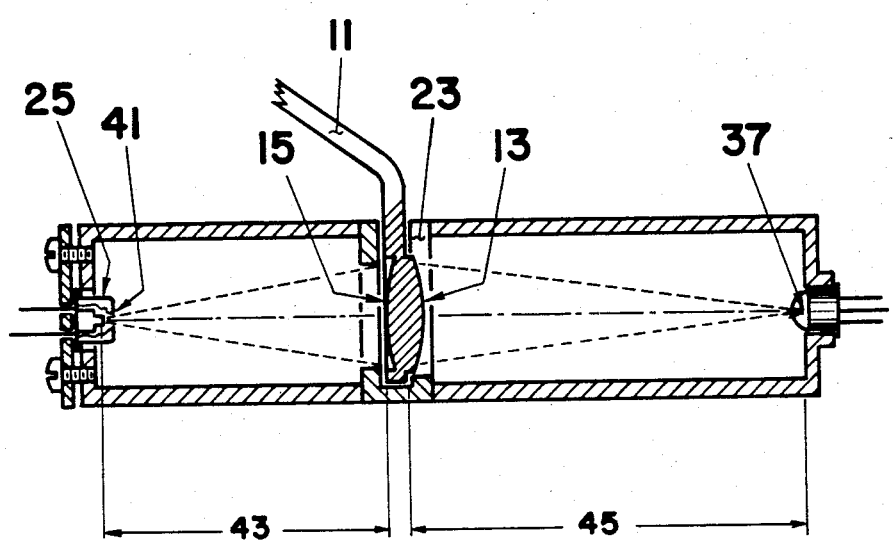
FIG. 3 shows an embodiment of the optical system, in which the optical power is provided by the sampling pellet alone.

The light gathering and focusing function performed in the embodiment of FIG. 2 by the collimating lens 29 and the refractive element of the sampling pellet 11, respectively, may be combined to be performed by the sampling pellet alone, as shown in FIG. 3. In this preferred embodiment of the optical system, the power of the refractive element of the sampling pellet 11 is entirely determined by the curvatures of the sampling surface 13 and the back surface 15 and the refractive index of the plastic in which the pellet is formed. These values are chosen such that the sampling pellet will form a sharp image of the luminous junction of the solid state emitter 25 at the surface of the detector 37, when the sampling pellet is separated by the conjugate distances 43 and 45 from the emitter 25 and the detector 37, respectively. For example, curvatures of 0.02500 mm$^{-1}$ (sampling surface) and 0.01667 mm$^{-1}$ (back surface) are appropriate. In practice, it can be easily arranged that the diameter of the emitting area 41 is substantially smaller than the diameter of the sensitized area of the detector 37. For example, an emitting area of 90-100 m diameter and a detecting area of 200-400 m diameter are suitable. Two benefits are derived from this fact. First, the conjugate distance 43 is shorter than the conjugate distance 45, resulting in a magnification of the source image on the detector, and in maximizing the amount of radiation utilized from the source; and second, the effect of certain residual optical aberrations of the sampling pellet will not result in a loss of light at the detector, since its active area is large enough to collect light which misses the ideal focal spot by a small margin. The size of the active area of the detector should be chosen to satisfy the conditions outlined above, but not larger. Residual aberrations of optical elements molded in plastic can be held to a minimum, which is well matched to the instrumental requirements.

Figure 4:
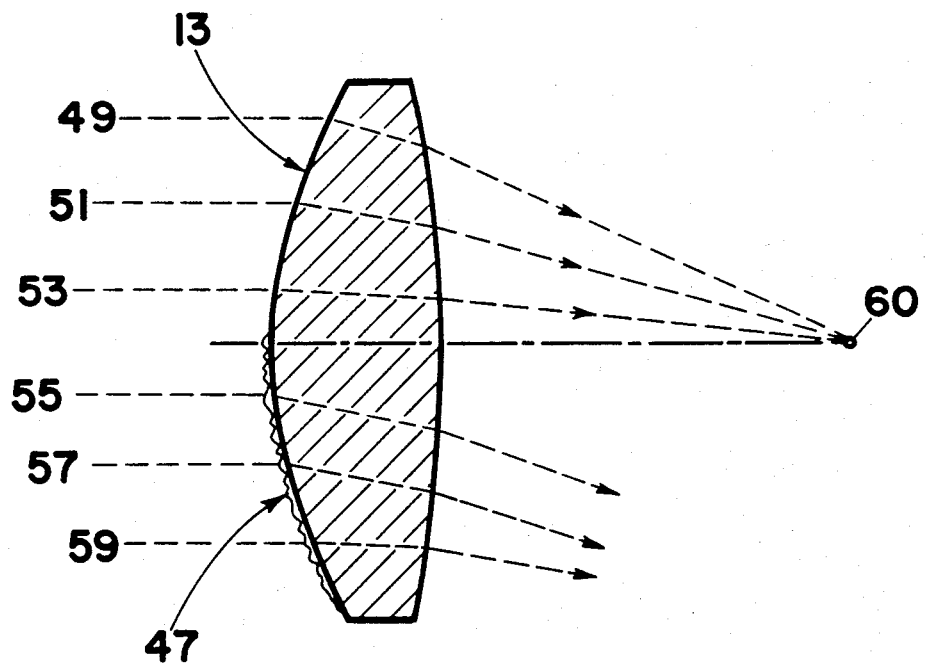
FIG. 4 is a schematic illustration of light rays affected by a clean or oily optical surface.

To perform a measurement, a clean sampling pellet 11 is inserted into the receptacle of the instrument. The sampling pellet has preferably been stored in a protective foil wrapping, which protected the optical surfaces from abrasion or contamination until the time of use. When the emitter 25 is turned on, nearly all radiation propagating through the pellet 11 is focused upon and received by the detector 37, resulting in a maximal photocurrent. This photocurrent level represents the value of a "clean" (dry) sample. An appropriate adjustment of the detection circuit may then be made to cause the indicator to read 100% signal, as will be discussed hereinafter. The sampling pellet is now withdrawn from its receptacle and pressed against an area of the skin, the oiliness of which is to be determined. As shown in FIG. 1, the handle of the sampling pellet is bent at a location 17 to prevent the fingers of the operator holding the grip area 19 from interfering with the sampling, while pressing the sampling surface 13 against the client's skin. On contacting the skin, oil present at the surface will be transferred to the sampling surface and forms there microscopic droplets of varying size or a film of irregular thickness. This surface coating affects the optical performance of the sampling surface in a variety of different ways. This is schematically illustrated in FIG. 4, where an aspheric sampling surface 13 is shown to intercept a beam of collimated light, represented by the rays 49, 51, 53, 55, 57 and 59. The lower part of the surface has been in contact with the skin and retains an irregular coating of oil 47, which forms a minutely corrugated buildup. Rays 49, 51 and 53 enter the clean part of the sampling surface and are refracted by it towards the lens' focal point 60 on the optic axis, where, in an analyzing instrument, the light detector would be located. However, rays 55, 57 and 59 which enter the oily part of the sampling surface are bent into different directions by virtue of refraction, total internal reflection (TIR), and scattering. These rays therefore are not directed to the lens focal point 60, and consequently would miss the light detector.

The magnitude of these effects of surface "contamination" is large, and may be better appreciated if it is remembered that a distortion of an optical surface by an amount equal to only a few wavelengths of the light can cause an appreciable wavefront deformation, which, in a focusing system, will result in significant decentration of the focused energy. Thus, this new system is particularly well suited for the measurement of skin oiliness, since tests have shown that a large percentage of the tested population indicated only rather slight skin oiliness. Prototype instruments involving the "ground-glass" sampling technique have been generally insensitive to low skin oil concentration. The presently disclosed device, which samples with an optically smooth surface and concentrates the incident light onto a detector, overcomes this deficiency, and responds well to the presence of even very small amounts of skin oil. Thus, after a skin oil sample is obtained by contacting the sampling pellet 11 to the skin, the pellet is once again inserted into the receptacle 23 of the analyzing apparatus, and due to the aforementioned effects of defocusing, the amount of radiation still reaching the detector is greatly reduced by the surface contamination of the sampling pellet. The correspondingly reduced photocurrent from the optical detector provides a measure of skin oiliness, when compared to the photocurrent obtained from a clean sample.

Another embodiment of the sampling pellet 11 is shown in FIG. 5. In this embodiment, the sampling surface 63 is raised, while the back surface 65 forms a circular recess, as seen in FIG. 6. Both surfaces are optically flat. When inserted into the receptacle of the corresponding optical system, the edge of the recess 67 forms the aperture stop of the system. The optical arrangement for this kind of sampling pellet is shown in FIG. 7. Since the plano-parallel surfaces 63 and 65 produce no refractive power, the instrument itself is equipped with a collimator lens 69 and an objective lens 61. The light in the space between these two lenses is parallel, so that the introduction therebetween of a plano-parallel sampling pellet does not change the ray geometry; the effect of surface contamination of the sampling surface, however, is the same as in the other preferred embodiments of the optical system, and the sensitivity of the measurement remains unchanged. This embodiment has the advantage that sampling pellets having two flat surfaces may be inexpensively produced with very consistent optical quality, by injection molding.

Figure 8:
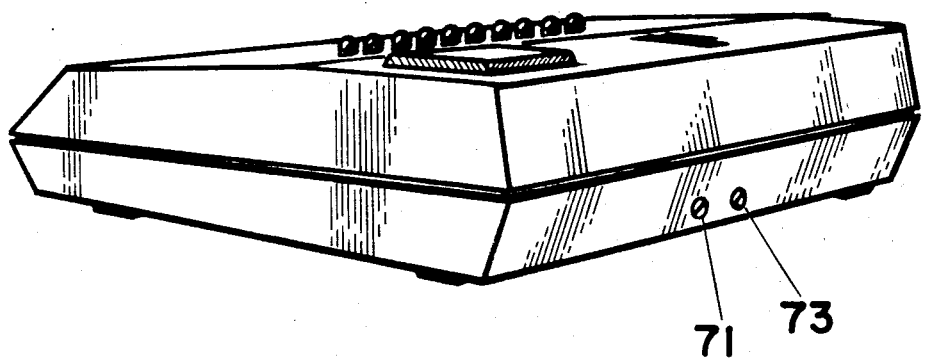
FIG. 8 is an oblique rear view of an instrument built in accordance with the present invention.
Figure 9:
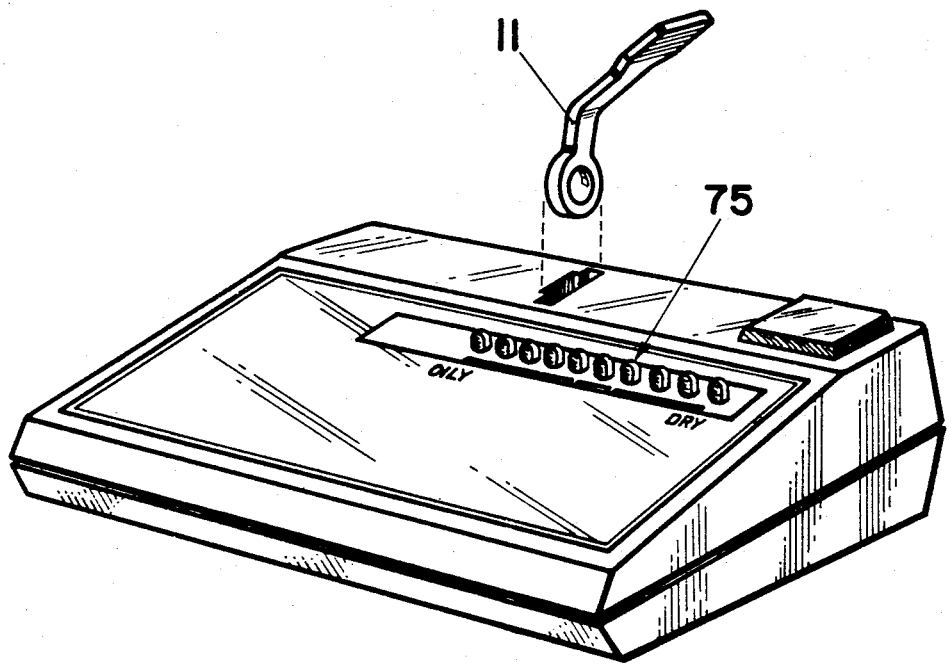
FIG. 9 is an oblique front view of an instrument built in accordance with the present invention.

In order to overcome the problem of quantifying the degree of skin oiliness in physical units of measurement, a preferred embodiment of the actual analyzing apparatus shown in FIG. 8 and FIG. 9 is equipped with two trim adjustments. First, a control labeled "gain" 71, is provided to set the indicator instrument to read 100% when a clean sample is in the receptacle. The indication in the instrument shown in FIG. 9 is given in the form of a light-emitting diode array 75. Then, a control labeled "spread" 73 is available to set the indicator to zero, after a sampling pellet is inserted, which corresponds to the highest degree of oiliness it is desired to indicate. The spread adjustment provided on instruments built in accordance with the present invention covers the range of 0.15 to 3.65 as the ratio between maximum and minimum photocurrent, while measured spread on actual test persons seems to fall near the ratio of 1.5/1 between the dryest and the oiliest specimen.

Figure 10:
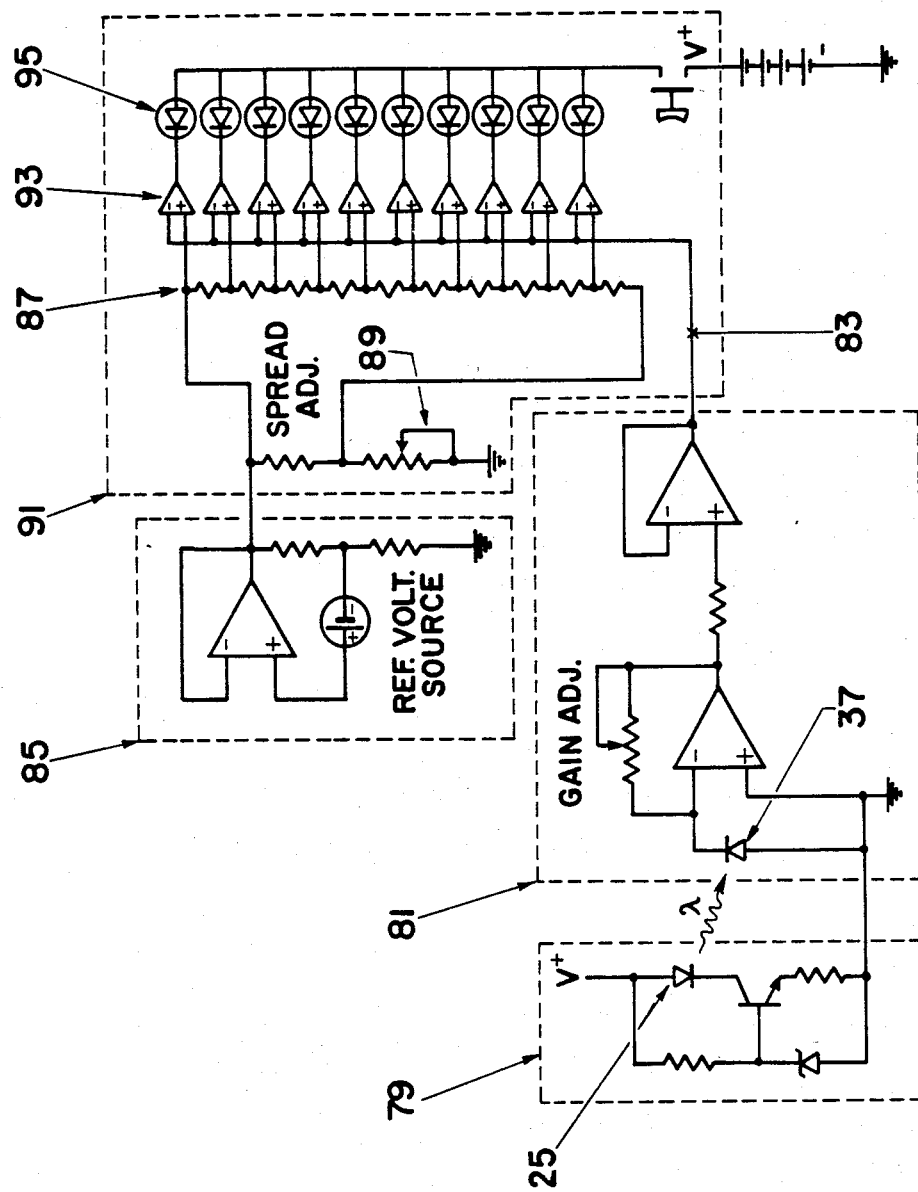
FIG. 10 shows a detector and display circuit used in the system.

One circuit embodiment suitable for use in any of the described embodiments of the instrument is given schematically in FIG. 10, in which a regulated current source 79 drives the infrared emitter 25. An amplifier 81 with variable gain converts the photocurrent from the detector 37 into a signal voltage 83. A stable reference voltage is generated by a voltage source 85, and applied across a resistor divider string 87. The magnitude of this reference voltage is set by a "SPREAD" adjustment resistor 89. An indicator circuit includes the resistor divider string 87, ten voltage comparators 93 and the ten associated indicator lamps 95. After appropriate adjustment of the GAIN and SPREAD resistors, insertion of a clean sampling pellet will produce an illumination of the topmost lamp, while a maximally oily pellet will cause illumination of the bottommost lamp; other values of oiliness will illuminate intermediate lamps.

I claim:
1. A method of measuring the degree of oiliness of the skin comprising the steps of:
 contacting the skin with a sampling pellet having optically smooth opposing surfaces, to impart oil from the skin onto one of said surfaces;
 removing said pellet from contact with the skin;
 directing an optical beam from an optical source through said sampling pellet;
 converging said optical beam onto an optical detector, said sampling pellet comprising a lens having oppositely curved surfaces so that said lens itself converges said optical beam onto said detector; and measuring the intensity of said converged optical beam to produce an indication of the degree of oiliness of the skin.

2. Apparatus for measuring the degree of oiliness of the skin comprising:
  sampling means having optically smooth opposing surfaces, for imparting oil from the skin onto one of said surfaces upon contact of said surface with the skin;
  optical source means for directing an optical beam through said sampling means, after said sampling means has been removed from the skin;
  optical detector means for detecting the intensity of said optical beam, after said optical beam has passed through said sampling means, said sampling means comprising a lens having oppositely curved surfaces so that said lens itself converges said optical beam onto said detector means; and
  display means responsive to an output signal from said detector means for displaying an indication of the degree of oiliness of the skin.

3. Apparatus for measuring the degree of oiliness of the skin comprising:
  sampling means having optically smooth opposing surfaces, for imparting oil from the skin onto one of said surfaces upon contact of said surface with the skin, said sampling means having one curved surface and one flat surface;
  optical source means for directing an optical beam through said sampling means, after said sampling means has been removed from the skin;
  optical detector means for detecting the intensity of said optical beam, after said optical beam has passed through said sampled means;
  a collimating lens positioned adjacent said sampling means which together with said sampling means is for converging said optical beam onto said detector means; and
  display means responsive to an output signal from said detector means for displaying an indication of the degree of oiliness of the skin.

4. Apparatus for sampling the oiliness of the skin, comprising a sampling pellet having optically smooth opposing surfaces, one of said surfaces being brought into contact with the skin to transfer oil from the skin to that surface and at least one of said surfaces being a curved surface.

5. Apparatus for sampling the oiliness of the skin, comprising a sampling pellet having optically smooth opposing surfaces, said surfaces being oppositely curved, and one of said surfaces being brought ino contact with the skin to transfer oil from the skin to that surface.

* * * * *